(12) United States Patent
Liang

(10) Patent No.: US 6,786,235 B2
(45) Date of Patent: Sep. 7, 2004

(54) PULSED WIDTH MODULATION OF 3-WAY VALVES FOR THE PURPOSES OF ON-LINE DILUTIONS AND MIXING OF FLUIDS

(76) Inventor: Dong C. Liang, 4882 Ontario Street, Vancouver, British Columbia (CA), V5V 3H5

( * ) Notice: Subject to any disclaimer, the term of this patent is extended or adjusted under 35 U.S.C. 154(b) by 104 days.

(21) Appl. No.: 10/114,074

(22) Filed: Apr. 3, 2002

(65) Prior Publication Data

US 2002/0139425 A1 Oct. 3, 2002

Related U.S. Application Data

(60) Provisional application No. 60/280,852, filed on Apr. 3, 2001.

(51) Int. Cl.[7] .............................................. F16K 11/044
(52) U.S. Cl. .............................. 137/625.4; 137/625.41; 251/129.05; 422/81; 422/103
(58) Field of Search ......................... 137/625.4, 625.41

(56) References Cited

U.S. PATENT DOCUMENTS

| | | | | |
|---|---|---|---|---|
| 4,063,077 A | * | 12/1977 | Wright | ........................ 700/265 |
| 4,487,333 A | * | 12/1984 | Pounder et al. | ................ 222/54 |
| 4,807,665 A | * | 2/1989 | Schiel | ...................... 137/625.4 |
| 5,540,668 A | * | 7/1996 | Wilson et al. | ............... 604/248 |
| 5,646,727 A | | 7/1997 | Hammer et al. | |

* cited by examiner

Primary Examiner—Stephen M. Hepperle (57) ABSTRACT

This invention relates to an apparatus comprising a switchable, 3-way valve device that delivers a constant flow rate stream of solution mixture to a chemical analysis instrument. The dilution valve is capable of mixing two input streams of solutions, at any dilution ratio from 0% to 100%, into a single output stream solution mixture. The dilution valve contains a switchable gate inside the 3-way T-junction, and the switching of this gate is controlled by pulsed width modulation of the power supply.

This invention also relates to methods involved in the delivery of solution mixtures to chemical analysis instruments, including on-line calibration from a single standard solution, on-line dilution from a single sample solution, and on-line standard addition from a single standard solution and a single sample solution.

10 Claims, 9 Drawing Sheets

PULSED WIDTH MODULATION OF 3-WAY VALVES FOR THE PURPOSES OF ON-LINE DILUTIONS AND MIXING OF FLUIDS

RELATED APPLICATIONS

This application claims the benefit of prior filed provisional application, Application No. 60/280,852 filed on Apr. 3, 2001.

FIELD

This invention relates to a system for accurately and quickly diluting and mixing fluid samples using a 3-way valve and pulse width modulation, such that the proportion of each fluid in the mixture can be accurately known. In particular, this invention relates to a system for delivering such fluid samples to a chemical analysis instrument.

BACKGROUND OF THE INVENTION

Dilution is the act of taking a concentrated fluid and making it less concentrated by mixing it with another, different fluid (a diluent). The diluent is usually a fluid whose composition, concentration, and other physical and chemical properties are all well known. A common diluent is water, $H_2O$. Ideally, there are no chemical or physical reactions between the diluent and concentrated fluid when mixed. When diluting a concentrated fluid, it is essential to know the degree to which the original fluid is diluted in order to be able to relate the diluted fluid to the original concentrated fluid. For example, it's critical to a chemical analysis to know whether the original concentrated fluid was diluted to 5% or to 95% of its original concentration.

Conventionally, mixing and dilution systems utilize pipettes or pumps (or some other means of moving fluids) to deliver different fluids to a mixing junction. To mix two fluids, the fluids are delivered to a T-junction or Y-junction (through separate input channels) where they are mixed and then exit the junction through a single output channel. These types of systems use linear power delivery to control the amount of fluid that is allowed to enter the mixing junction through each input channel. A problem with these linear control devices is that the efficiency of the electronic control components is poor when operated at mid-range power levels, and power is lost as heat in the components of the electrical circuits controlling the device. More importantly, the linear power delivery is not accurate enough for high-precision mixing applications when very small volumes are involved.

U.S. Pat. No. 5,646,727 (July 1997), issued to Hammer et al., is a specific example of a linear method of mixing and diluting. Hammer et al use peristaltic pumps to deliver sample solutions to a 3-way T-junction or a 4-way X-junction. With the T-junction setup, there is a sample solution connected to an input channel and a peristaltic pump is used to deliver the fluid to the junction. There is a diluent solution connected to the other input channel (with no pump) and the output channel is connected to a nebulizer of a spectroscopic instrument. With the X-junction setup, there is an additional input channel to which a standard solution is connected with a peristaltic pump for fluid delivery to the junction. The nebulizer operates by aspiration and so there is always a drop in pressure between the junction and the nebulizer. Under proper operating conditions, this vacuum pressure can be used to draw up diluent and pull it through the junction. The amount of sample or standard delivered to the junction depends on the pumping speed of the peristaltic pumps. The electrical power supplied to these pumps is delivered by the linear method described above.

Just as traditional power delivery methods are called "linear", traditional methods of mixing and diluting fluids can also be called "linear". Traditional methods use a T-junction to mix and dilute fluids, and allow both of the two input fluids to flow freely and unimpeded into the junction at the same time. That is, the junction in which the fluid mixing occurs has no valves to control the flow of fluids into it. Traditional methods rely on the control of the flow rates of the two input fluids. In this way, control of how much of each fluid enters the junction per unit time is achieved, and therefore control the degree of mixing or diluting is achieved. This method can be considered "linear" because the controlling method is the linear control of the flow rates of the input fluids (i.e. the flow rates of the pump are adjustable anywhere between LOW and HIGH rates).

Traditionally, 3-way valves have the ability to select which input fluid path flows through the valve (i.e.ON/OFF control). However, presently there is a need for a 3-way valve that may be used for the purpose of mixing and/or diluting fluid samples, in addition to basic fluid flow selection. As a result, it is an object of the present invention to use a 3-way valve for the purpose of mixing and/or diluting fluid samples.

It is a further object of the present invention to provide a system that integrates the pulse width modulation (PWM) method of power delivery with a 3-way valve apparatus for delivering a diluted sample (of varying degrees of dilution) to a sample introduction apparatus of a chemical analysis instrument, along with methods for on-line calibration and sample analysis.

SUMMARY OF THE INVENTION

The present invention is a 3-way valve with two inlet ports, and an outlet port. The 3-way valve controls which inlet port has an open path to the outlet port via a switchable gate located inside the junction of the three ports. The gate is controlled by an electrical input into a solenoid coil, such as the 3-way solenoid valve provided by Lee Co. (model # LHDA 0523112H), which enables the gate to be switched between the two inlet ports to provide an open path for one or the other, but never both at the same time. Two different fluids are connected to the inlets and introduced into the valve. The fluids are introduced into the valve either by suction from the outlet port or by pressure applied on the inlet fluid reservoirs, the electrical input is by pulse width modulation (PWM).

The flow of a fluid through the 3-way valve junction is either ON or OFF. The free and unimpeded flow of both fluids (simultaneously) into the outlet port is not allowed. Fluids are only allowed to flow separately into the outlet port (one at a time). If one fluid is flowing into the outlet port (it is ON) then it is flowing in at a constant flow rate and the other fluid is not flowing into the outlet port at all (it is OFF). There is no intermediate state between ON and OFF, effectively resulting in a digital system.

The dilution of a concentrated solution is achieved is by feeding the concentrated sample solution into one inlet port (the sample path) and feeding a diluent into the other inlet port (the diluent path). One of the two inlet ports is opened to allow fluid to flow through the valve junction and into the outlet port, while the gate is rapidly switched ON and OFF between the two ports. Over a period of time where many ON/OFF cycles are completed, the flow of a fluid through the 3-way valve takes on a "pulsed" nature. The main controlling factors that affect dilution using this method are the frequency with which the inlet paths are switched, the duration of each ON and OFF period for each inlet fluid, and the constant flow rate (or pressure) of each inlet fluid.

This system is capable of passing gaseous or liquid samples through the 3-way valve, and the degree of dilution can vary between 0–100%. The invention is applicable to any chemical analysis instrument or measuring technique that can facilitate a liquid or gaseous sample.

BRIEF DESCRIPTION OF THE VIEWS OF THE DRAWINGS

Further features and advantages of the invention will be apparent from the following detailed description, given by way of example, of a preferred embodiment taken in conjunction with the accompanying drawings, wherein:

FIG. 2b is a diagram of the 3-way valve and gate comprised of an internal solenoid switch blocking the other path as illustrated in FIG. 2a;

FIG. 5 is a schematic diagram of the distribution manifold. The view is head on;

DETAILED DESCRIPTION OF THE INVENTION

Figure 1:
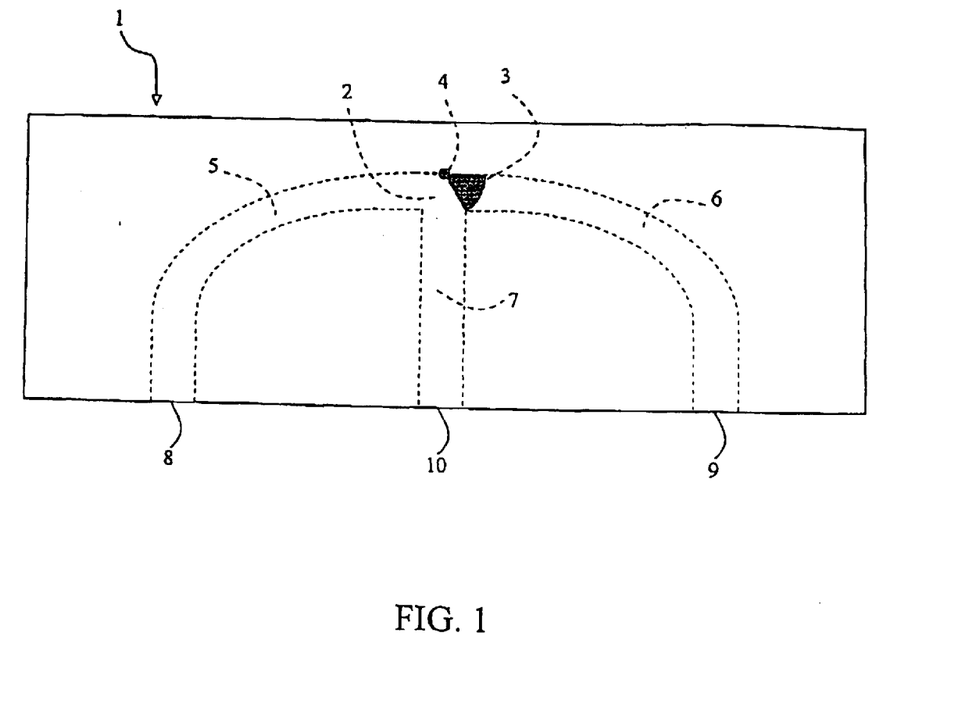
FIG. 1 is a schematic diagram of the 3-way valve with the gate.

Referring to FIG. 1 a schematic view of a 3-way valve 1 is shown. The 3-way valve comprises a switchable gate 3 on a hinge 4 inside the T-junction 2 of the 3-way valve 1. Switchable gate 3 that is powered by PWM power delivery.

The 3-way valve 1 has three ports, two inlet ports 8 and 9 and one outlet port 10, with inlet paths 5 and 6 and outlet path 7, which intersects at a T-junction 2. Each inlet port 8 and 9 allows a solution to enter into the 3-way valve 1. The outlet port 10 is ultimately directed into the sample introduction apparatus of a chemical analysis instrument.

The position of the gate 3 inside the T-junction 2 of the 3-way valve 1 determines which inlet path 5 and 6 through the valve is open. The gate 3 has only two possible positions: either ON or OFF. If the gate is ON, then one inlet path through the valve is completely open and the other path is completely closed. If the gate is OFF, then the gate position is switched and the previously closed inlet path is now completely open and the previously open inlet path is now completely closed.

The gate 3 switches between the ON and OFF positions to alternately allow the fluid flows from the two inlet paths 5, 6 to flow through the junction 2 and through the outlet path 7 and out through the outlet port 10. In FIG. 1, inlet path 5 is open (ON), and inlet path 6 is closed (OFF).

An important feature of the 3-way valve 1 is that the volume and flow rate of solution through the outlet port 10 is constant, regardless of which of input paths 5 and 6 is open provided that the two input solution pressures are equal. The volume flow capacity through the 3-way valve 1 is dependant on the diameter of the inlet paths 5 and 6. The fluids are introduced into the 3-way valve 1 either by suction from the outlet port 10, by an apparatus such as a nebulizer, or by pressure applied on the inlet fluid reservoirs (not shown).

Thorough mixing of the inlet solutions that are alternately allowed to flow through the 3-way valve 1 is accomplished as the outlet solution mixture travels through the outlet path 7 of the 3-way valve 1. As well, effective outlet solution mixing is accomplished to a large extent by high frequency of switching of the gate 3.

Internal Solenoid Coil

Figure 2A:
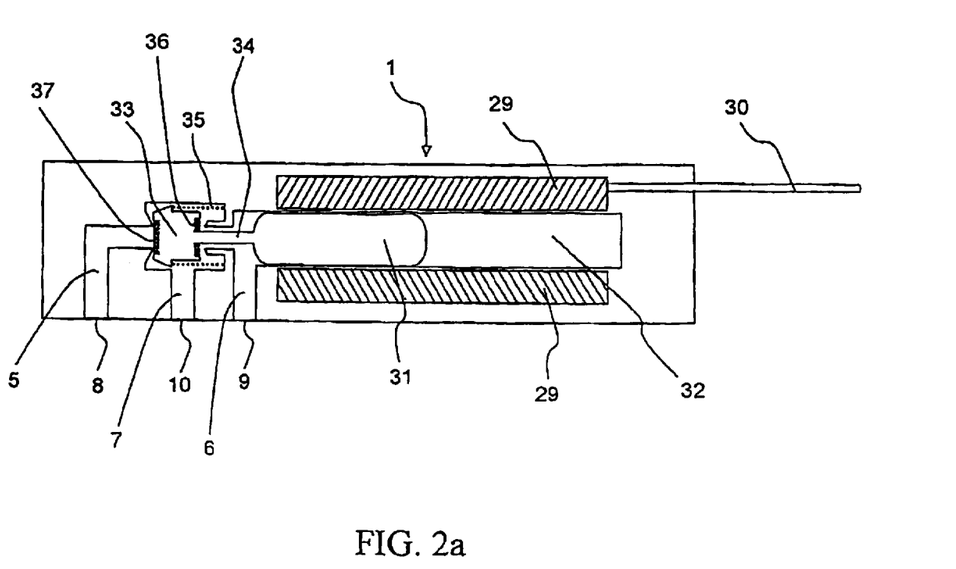
FIG. 2a is a diagram of the 3-way valve and gate comprised of an internal solenoid switch blocking one path.
Figure 2B:
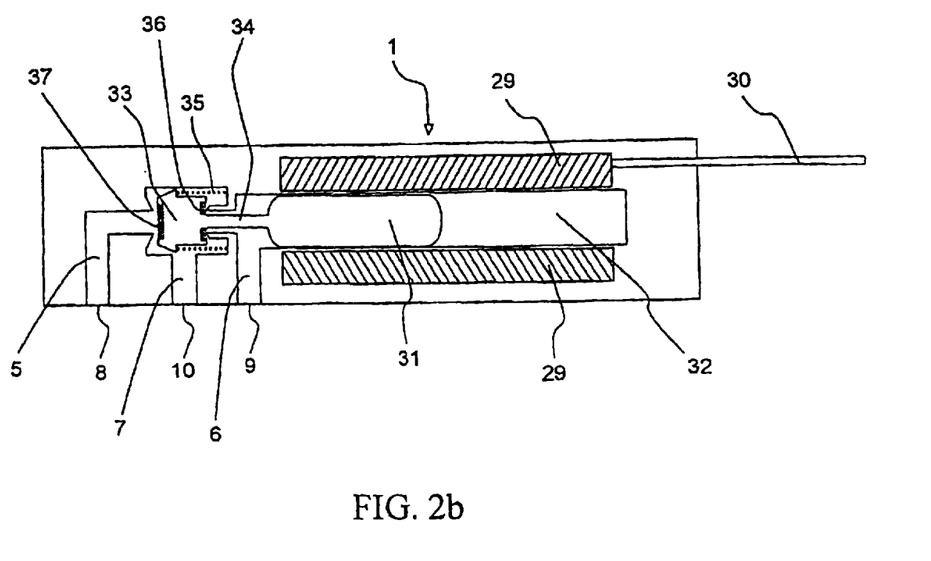

Referring to FIGS. 2a and 2b in the preferred embodiment, a controller (not shown) that is attached to the gate 3 of the 3-way valve 1 causes an internal solenoid to switch.

Inside the 3-way valve 1, there is a single coil 29 of electrically conducting wire. Each of the two ends of this coiled wire 29 are connected to separate electrical contact leads 30, which extend out of the body of the valve device 1 for wiring connection to the controller. There is a hollow chamber 32 inside the wire coil 29. Inside the chamber 32 is a magnetic rod 31. The rod 31 is shorter than the length of the chamber 32, and the rod's outer diameter is slightly smaller than the inner diameter of the chamber. Therefore, the rod can move freely back and forth along the length of the chamber. At one end (the left end in the figure) of the rod 31 is a smaller diameter arm 34, and at the end of this arm is the solenoid head 33. When electrical current is passed through the conducting wire of the coil 29, a magnetic field is generated inside the coil (and thus inside the hollow chamber 32). The magnetic bar 31 that is housed inside the chamber 32 has a force exerted on it by the generated magnetic field. This force causes the magnetic bar 31 to move horizontally inside the chamber 32, along the length of the chamber. The direction of the forced movement of the bar depends on the polarity of the electrical current passed through the coil 29.

There are three paths (5, 6, and 7) through the 3-way valve 1, and they all meet at a T-junction 2. Inside the T-junction is a coil spring 35 that presses on a lip of the solenoid head 33, and forces it against the opening to inlet path 5. A silicon seal 37 on the solenoid head 33 seals off inlet path 5 and prevents any fluid flow. Therefore, in this "normal" position, fluid flow is only allowed through inlet path 6 to outlet path 7.

Referring to FIG. 2b, when current is passed through the coil 29, the generated magnetic field forces the magnetic bar 31 to move the right inside the chamber 32. This compresses the spring 35 and moves the solenoid head 33 to the right. This releases the seal made by seal 37 against the opening to channel 5. When the magnetic bar has moved far enough to the right, another silicon seal 36 on the solenoid head 33 will form a seal against the opening to inlet path 6, thus preventing any fluid flow. In this "pulsed" position, fluid flow is only allowed through inlet path 5 to outlet path 7.

When there is no electrical current flowing through the coil of wire 29, then the 3-way valve 1 is in its "normal" position, and fluids can only flow through inlet path 6 to outlet path 7. When there is electrical current flowing through the coil of wire 29, then the 3-way valve 1 is in its "pulsed" position, and fluids can only flow through inlet path 5 to outlet path 7.

The physical design and characteristics of the solenoid may be modified according to the needs of any particular valve.

Frequency of Swithable Gate

The rate at which the gate switches between ON and OFF positions is determined by the operating frequency of the PWM electrical impulses controlling the gate position. At 50 Hz, for example, the gate will complete 50 cycles per second. One cycle of the gate occurs when it switches from OFF to ON and back to OFF again.

The duration of each position (i.e. how long the gate remains in the ON or OFF position) is determined by the duty cycle of the PWM power delivery. At 20%, for example, the gate will remain ON for 20% of the total time of each cycle and OFF for the remaining 80%. Note that at a 0% duty cycle the gate will remain ON for 0% of the time and OFF for 100% of the time. This would correspond to either a 0% dilution or a 100% dilution, depending on which inlet ports the sample and diluent solutions were connected to.

Figure 3:
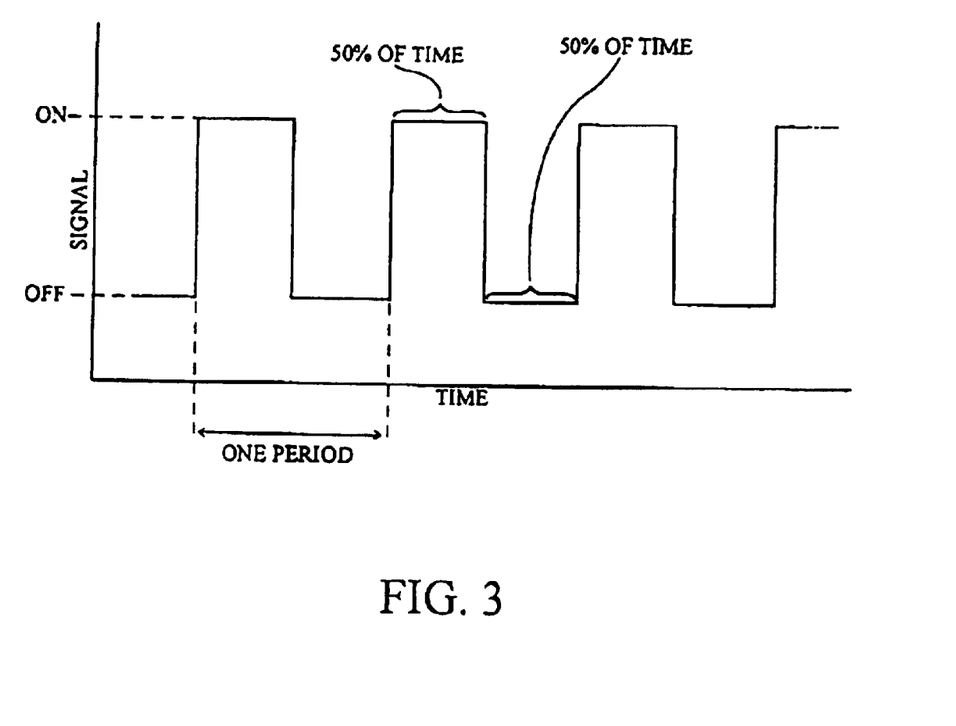
FIG. 3 is a graph of a signal versus time for a pulse width modulated signal with a 50% duty cycle.

Referring to FIG. 3 a signal versus time graph of PWM power delivery for a 50% duty cycle. The square wave in the graph has only two possible signal intensities: ON or OFF. One period (one full cycle) is indicated on the graph. For one period of a 50% duty cycle, the length of time that the signal is ON is 50% of the total time of the period. At an operating frequency of 50 Hz, for example, the length of time of one period is 1/50th of a second, or 0.02 seconds. So, at an operating frequency of 50 Hz and a duty cycle of 50%, the gate 3 would remain ON for 0.01 seconds of each period.

Figure 4:
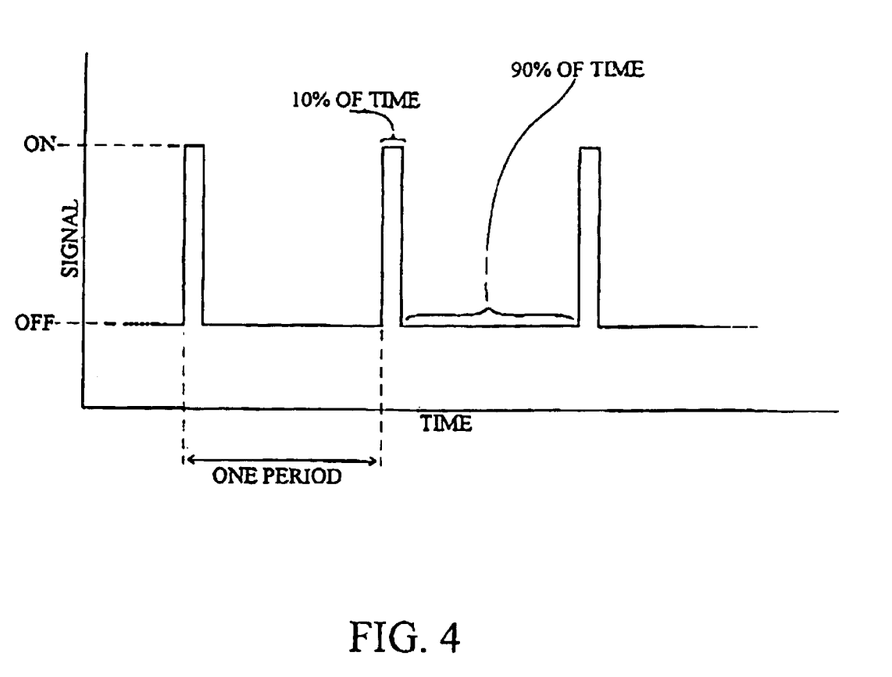
FIG. 4 is a graph of a signal versus time for a pulse width modulated signal with a 10% duty cycle.

Referring to FIG. 4 is a signal versus time graph of PWM power delivery for a 10% duty cycle. One period (one cycle) is indicated on the graph. Note that the total length (or time) of the period is the same as in FIG. 3. For one period of a 10% duty cycle, the length of time that the signal is ON is 10% of the total time of the period. For example, consider an operating frequency of 50 Hz. There would be 50 cycles completed each second, so the total duration of each cycle would be 0.02 seconds (1 second/50 cycles). With a duty cycle of 10%, the gate would remain ON for 0.002 seconds (10% of 0.02 seconds) of each period and OFF for the remaining 0.018 seconds (90% of 0.02 seconds) of the 0.02 seconds period.

Distribution Manifold

Figure 5:
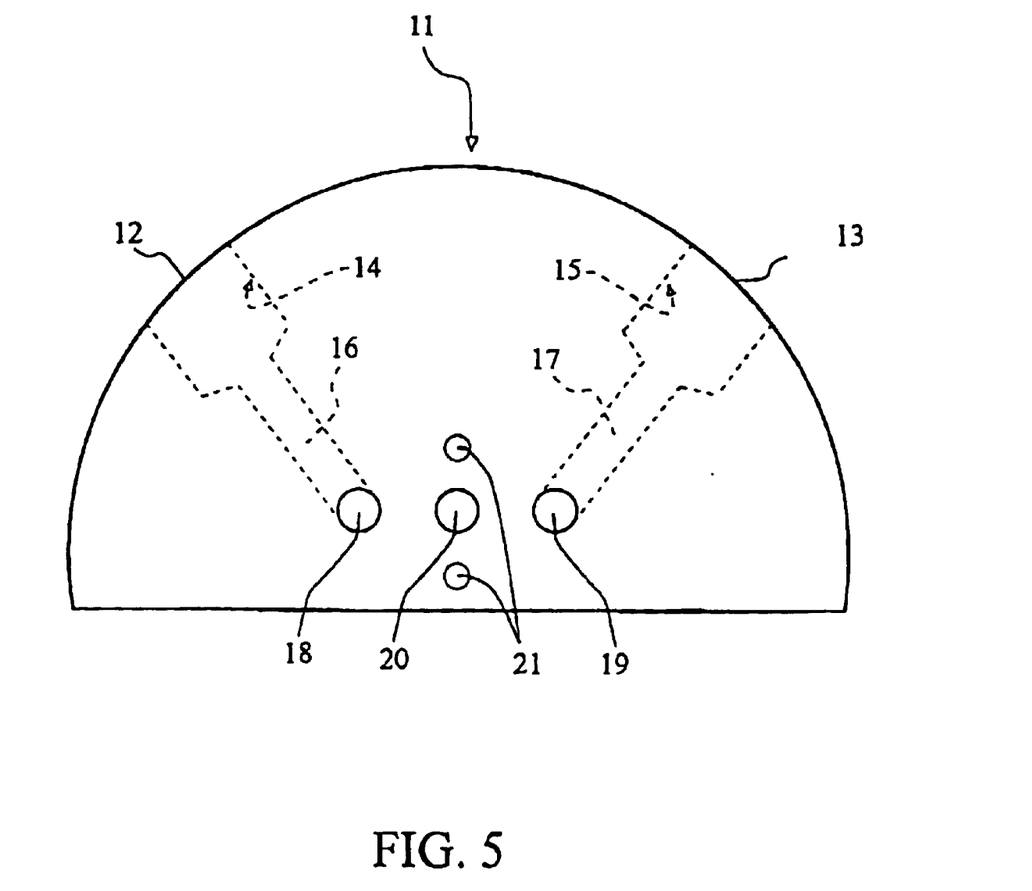
Figure 6:
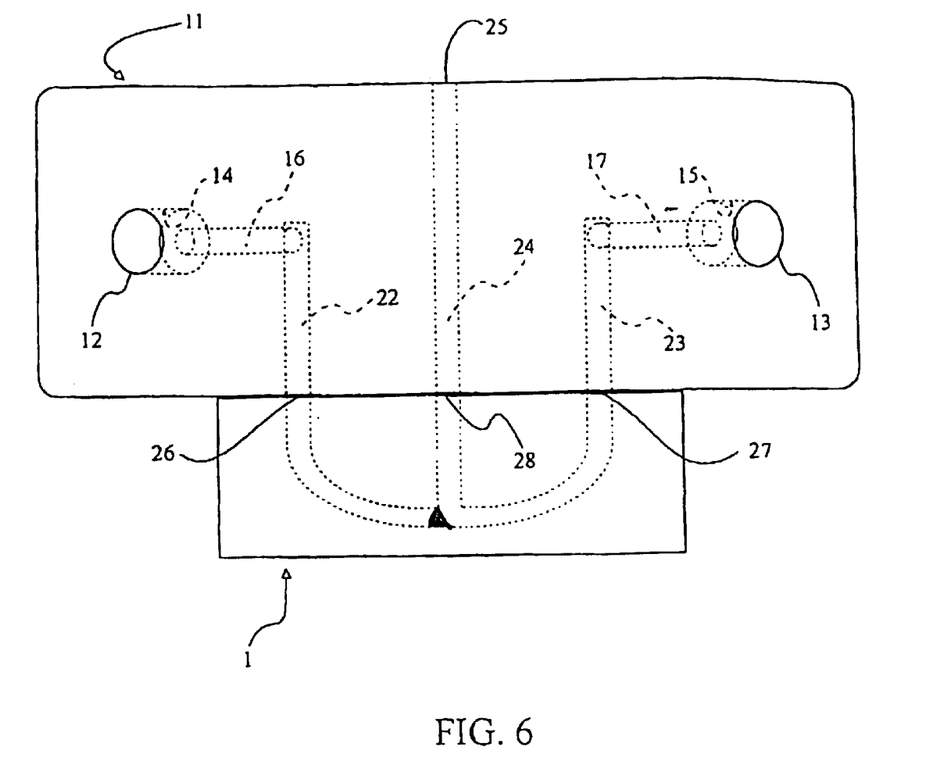
FIG. 6 is a schematic diagram of the distribution manifold and dilution valve mounted together. The view is from above.

Referring to FIG. 5 and FIG. 6 in the preferred embodiment the 3-way valve 1 is connected to a distribution manifold 11 that performs dual functions, the first of which is to deliver two supply streams into the 3-way valve 1 (sample and diluent solutions) and the second of which is to deliver the output stream from the 3-way valve 1 into a sample introduction apparatus of a chemical analysis instrument.

FIG. 5 a schematic diagram of the frontal view of the distribution manifold 11. FIG. 6 shows a schematic diagram of the top view of the distribution manifold 11 with the 3-way valve 1 aligned and in position on the frontal face of the manifold. The figures show three, 3-way valve portholes in the manifold. The center porthole 20 aligns with the output port 10 of the 3-way valve 1. The hole 20 is bored all the way through the manifold, forming an output channel 24 from the front through to the back. When the output fluid from the 3-way valve 1 exits the valve, it enters the central porthole 20 in the manifold (where the manifold and dilution valve are aligned against each other 28), travels through the bored channel 24, and exits through the back of the manifold 25 where it is delivered to the sample introduction device of a chemical analysis instrument (in most cases, tubing will connect the output of the manifold to the sample introduction device). Further mixing occurs as the output fluid flows through the output channel 24 of the distribution manifold 11, and through the tubing connecting the distribution manifold output 25 to the chemical analysis instrument, such as flame atomic absorption spectrometry (FAAS), vapor/hydride generation atomic absorption spectrometry (VGAAS), inductively coupled plasma (ICP), inductively coupled plasma mass spectrometry (ICPMS), gas chromatography (GC), and high performance liquid chromatography (HPLC).

The other two portholes 18, 19 in the front of the manifold 11 (on either side of the central porthole 20) align 26, 27 with the input ports 8, 9 of the 3-way valve 1. These portholes 18 and 19 are bored a distance into the manifold (forming channels 22, 23), but not all the way through. On the top (rounded) surface of the distribution manifold 11 are two input ports 12, 13 with threaded holes 14, 15 for the connection of fittings for the tubing carrying the input fluids. In each of these threaded holes, there are holes 16, 17 bored down through the manifold to intersect with the bored channels 22, 23 from the portholes aligned 26, 27 with the input valves. The two channels 16, 17 intersect at right angles with the bored channels 22, 23. Fluids to be mixed and diluted in the 3-way valve 1 are delivered to the valve via tubing connected to the fittings that thread into the threaded holes 14, 15 in the input ports 12, 13 of the distribution manifold 11, through the bored channels 16, 22 and 17, 23, through the junctions 26, 27 between the manifold and valve, through the input channels 5, 6 in the valve, through the T-junction 2, out through the output channel 7, through the junction 28 between the manifold and valve, through the bored output channel 24, and out of the manifold 25 and into the sample introduction device of the chemical analysis instrument.

The 3-way valve 1 is affixed to the distribution manifold 11 with small screws into threaded holes 21 in the frontal face of manifold. The manifold 11 itself is attached to the sample introduction device by screws as well (holes through the manifold are not shown).

FIG. 6 shows how the bored channels from the threaded input ports 12, 13 connect to the portholes 18, 19, 20 on the frontal face of the manifold 11 (through the junctions 26, 27, 28 formed between the manifold and dilution valve in FIG. 5).

On-line Calibrations and Standard Addition Techniques

The invention may also be used as a device for on-line calibrations of chemical analysis instruments. This function is easily accomplished by supplying a single stock standard solution (containing a known concentration of the species to be analyzed) into one input port 12 of the distribution manifold 11, and a diluent (such as water) into the other input port 13. The output mixture from the 3-way valve 1 can be anywhere from 100% standard solution to 0% standard solution (i.e. 100% water), by varying the duty cycle of the 3-way valve 1 gate switch 3. With this method, varying dilutions of the original standard solution (each diluted mixture having a known concentration) can be delivered to a chemical analysis instrument for calibration purposes.

As well, the invention may be used to perform on-line standard addition techniques for chemical analysis. This function is easily accomplished by again supplying a single stock standard solution (containing a known concentration of the species to be analyzed) to one of the input ports 12 of the distribution manifold 11. To the other input port 13 is supplied the unknown sample solution that is to be analyzed. Depending on the duty cycle of the 3-way valve 1, the unknown sample can be analyzed pure (i.e. 100% duty cycle) or it can be spiked with varying amounts of the standard solution. The unknown sample is then measured by the chemical analysis instrument multiple times (first as a pure sample and then with increasing numbers of spikes of the standard solution). When this technique, known as standard addition, is employed for chemical analysis the measuring instrument does not require any pre-calibration because the effects of the added standard solution (whose amount is accurately known) on the unknown solution (whose amount is not known) can be compared. The amount of the species of interest in the original unknown sample can interpolated from the data obtained from the multiple standard addition measurements.

Series Configuration of 3-Way Valve Device

Figure 7:
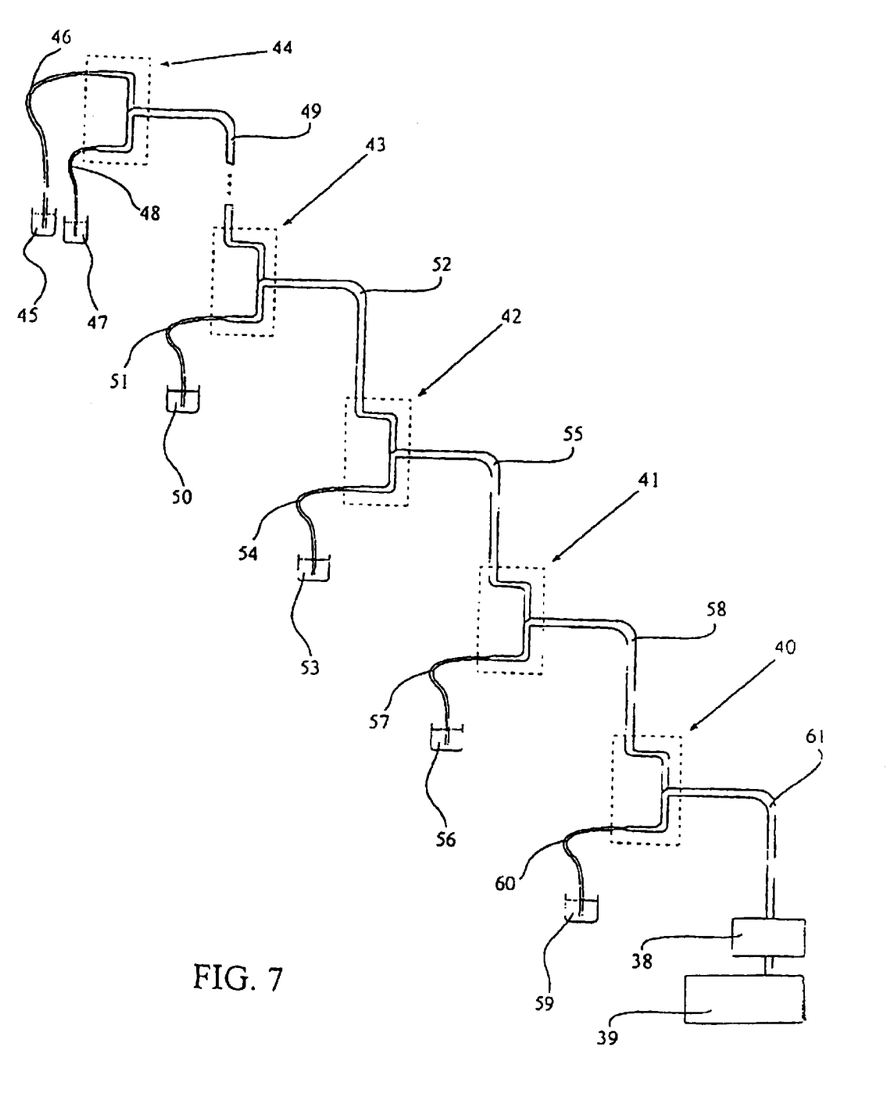
FIG. 7 is a schematic diagram of the 3-way dilution valve arranged in series.

FIG. 7 is a schematic diagram of multiple 3-way valves used in series configuration. FIG. 7 shows five 3-way valve devices setup in series, but the actual number is limited only by suction pressure. That is, the suction pressure exerted at the source must be sufficient to aspirate fluids from the most distant 3-way valve in the system. Note that each 3-way valve depicted in the figure is the same as the 3-way valve shown in FIG. 1.

A chemical analysis instrument 39 is connected to a nebulizer sample introduction device 38 that operates by aspiration. Therefore, this nebulizer provides suction that will aspirate fluids through the tubing and valve system. The nebulizer 38 is coupled to the first 3-way valve device 40 by tubing 61. One input port of this valve 40 is coupled by tubing 60 to a solution container 59. The other input port of the valve 40 is connected by tubing 58 to the output port of another 3-way valve 41. One input port of this valve 41 is coupled by tubing 57 to a solution container 56. The other input port of the valve 41 is connected by tubing 55 to the output port of another 3-way valve 42. One input port of this valve 42 is coupled by tubing 54 to a solution container 53. The other input port of the valve 42 is connected by tubing 52 to the output port of another 3-way valve 43. One input port of this valve 43 is coupled by tubing 51 to a solution container 50. The other input port of the valve 43 is connected by tubing 49 to the output port of another 3-way valve 44. One input port of this valve 44 is coupled by tubing 48 to a solution container 47. The other input port of the valve 44 is connected by tubing 46 to solution container 45.

An example of an application using such a series valve configuration would have solution containers 59, 56, 53, and 50 containing buffer solutions to be mixed with an unknown sample, solution container 47 containing a wash/diluent solution, and solution container 45 containing a sample solution.

It is not indicated in the figure, but the tubing 46 connected to the input port of the final 3-way valve 44 could be connected to an XYZ autosampler. The tubing 46 would then become a sampling tip that could be moved around by the autosampler and be dipped into various sample solution containers (such as microplates). This would add flexibility to aspirate multiple sample solutions without having to add more 3-way valves to the series.

Basically, there should be as many 3-way valves connected in series as there are common solutions that would be used in most of the dilutions. For example, if there are two buffer solutions and one diluent, then there should be at least three 3-way valve connected in series. One of the input ports on the final valve could be used as a sampling tip on an autosampler (if there are multiple sample solution containers), or it could be connected directly to a sample solution container (if it is the only sample solution to be analyzed).

1-Way Valves

Figure 8:
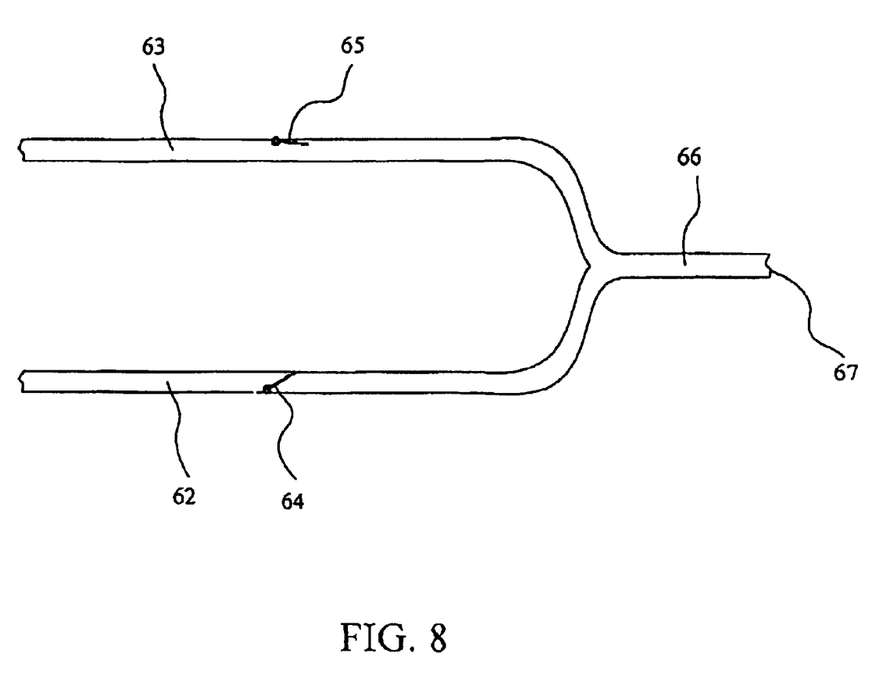
FIG. 8 is a schematic diagram of an alternative system using multiple 1-way valves.

FIG. 8 shows an alternate system using PWM control of valves for the purpose of mixing fluids. This system uses separate valves for each line of fluid flow to control the amount of fluid flowing into a mixing junction. In the figure, inlet tubing 63 has a 1-way valve 65 (in the ON position), and the other inlet tubing 62 has a 1-way valve 64 (in the OFF position). These two inlet tubes meet at a junction and become outlet tubing 66. The fluids from tubes 63 and 64 are mixed together in the junction and in tube 66, and exit the system through output 67. This system represents a modification of the mixing system in that it uses PWM of 1-way valves for the purposes of mixing fluids, rather than a 3-way valve.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to the description. It is therefore contemplated that the appended claims will cover any such modifications or embodiments as fall within the true scope of the invention.

What is claimed is:

1. A system for diluting and mixing fluid samples, comprising:
  (a) a three-way valve having a first inlet coupled to a first fluid source, a second inlet coupled to a second fluid source, an outlet, and a gate, said gate operative to switch said outlet from fluid communication with one of said first and second inlets;
  (b) a controller coupled to said gate, said controller operative to cause said gate to switch;
  (c) a pulse width modulation signal source operative to apply a pulse width modulation control signal to said controller and cause said gate to switch in response to each half-cycle of said pulse width modulation control signal; and
  (d) a nebulizer coupled to said outlet to serve as a flow inducing means operative to provide a constant rate of flow of said first and second fluids through said outlet.

2. The system according to claim 1, wherein said controller includes a solenoid coil coupled to said gate.

3. The system according to claim 1, wherein said gate switches at a frequency and duty cycle determined by the frequency and duty cycle of an input electrical signal.

4. The system according to claim 1, wherein switching of said gate is operative to allow mixing between said first and second fluids in said outlet.

5. The system according to claim 1, wherein said gate is positioned at a T-junction of said three-way valve.

6. The system according to claim 1, wherein said gate is positioned at a Y-junction of said three-way valve.

7. The system according to claim 1, wherein said first and second fluids are one of: liquid, gas, and a combination of liquid and gas.

8. The system according to claim 1, wherein said first fluid is a diluent and said second fluid is a sample.

9. The system according to claim 8, wherein said sample is received from an autosampler.

10. A system according to claim 1, further comprising a distribution manifold having:

(a) a first input coupled to said first inlet, said first input operative to supply said first fluid to said first inlet;

(b) a second input coupled to said second inlet, said second input operative to supply said second fluid to said second inlet; and (c) an output coupled to said outlet; said output operative to receive fluids from said outlet.

\* \* \* \* \*